United States Patent
Mennen

(10) Patent No.: US 8,377,399 B2
(45) Date of Patent: Feb. 19, 2013

(54) PROCESS FOR INCREASING THE CAPACITY OF AN EXISTING UREA PLANT

(75) Inventor: Johannes Henricus Mennen, Meijel (NL)

(73) Assignee: Stamicarbon B.V., Sittard (NL)

( * ) Notice: Subject to any disclaimer, the term of this patent is extended or adjusted under 35 U.S.C. 154(b) by 148 days.

(21) Appl. No.: 12/936,190

(22) PCT Filed: Mar. 30, 2009

(86) PCT No.: PCT/EP2009/053748
§ 371 (c)(1),
(2), (4) Date: Dec. 23, 2010

(87) PCT Pub. No.: WO2009/121843
PCT Pub. Date: Oct. 8, 2009

(65) Prior Publication Data
US 2011/0110826 A1     May 12, 2011

(30) Foreign Application Priority Data
Apr. 2, 2008 (EP) .................. 08006710

(51) Int. Cl.
*B01J 8/00* (2006.01)
*B01J 19/00* (2006.01)
*C07C 273/00* (2006.01)
*C07D 251/60* (2006.01)

(52) U.S. Cl. .......... 422/600; 422/129; 422/187; 564/32; 564/63; 564/66; 564/67; 564/68; 564/70; 564/71; 564/72; 544/201

(58) Field of Classification Search .......... 422/129, 422/187, 600, 608, 609; 564/1, 32, 63, 66–72; 544/1, 180, 194, 196, 200, 201
See application file for complete search history.

(56) References Cited

U.S. PATENT DOCUMENTS

| | | | |
|---|---|---|---|
| 6,118,023 A | 9/2000 | Jonckers et al. | |
| 6,150,555 A * | 11/2000 | Pagani et al. | 564/67 |
| 8,158,823 B2 * | 4/2012 | Zardi et al. | 564/67 |
| 2002/0035292 A1 * | 3/2002 | Mennen et al. | 564/67 |
| 2007/0282102 A1 * | 12/2007 | Brunengo et al. | 544/201 |

FOREIGN PATENT DOCUMENTS

| | | |
|---|---|---|
| EP | 0 598 250 | 5/1994 |
| WO | WO-96/20170 | 7/1996 |
| WO | WO-02/090323 | 11/2002 |
| WO | WO-2006/061083 | 6/2006 |

OTHER PUBLICATIONS

International Search Report for PCT/EP2009/053748, mailed on May 11, 2009, 3 pages.
Meessen, "Ulmann's Encyclopedia of Industrial Chemistry, UREA" (2005) pp. 13-19.

* cited by examiner

*Primary Examiner* — Walter D Griffin
*Assistant Examiner* — Natasha Young
(74) *Attorney, Agent, or Firm* — Morrison & Foerster LLP

(57) ABSTRACT

Process for increasing the capacity of an existing urea plant comprising a high-pressure urea synthesis section and one or more recovery sections, wherein next to the existing urea plant a urea production unit, comprising a high-pressure urea synthesis section and a medium-pressure recovery section, is installed, wherein a urea-containing stream is produced from ammonia and carbon dioxide and the urea-containing stream is sent to the existing urea plant where the urea-containing stream is further purified in the low-pressure recovery section.

13 Claims, 2 Drawing Sheets

PROCESS FOR INCREASING THE CAPACITY OF AN EXISTING UREA PLANT

CROSS-REFERENCE TO RELATED APPLICATIONS

Figure 1:
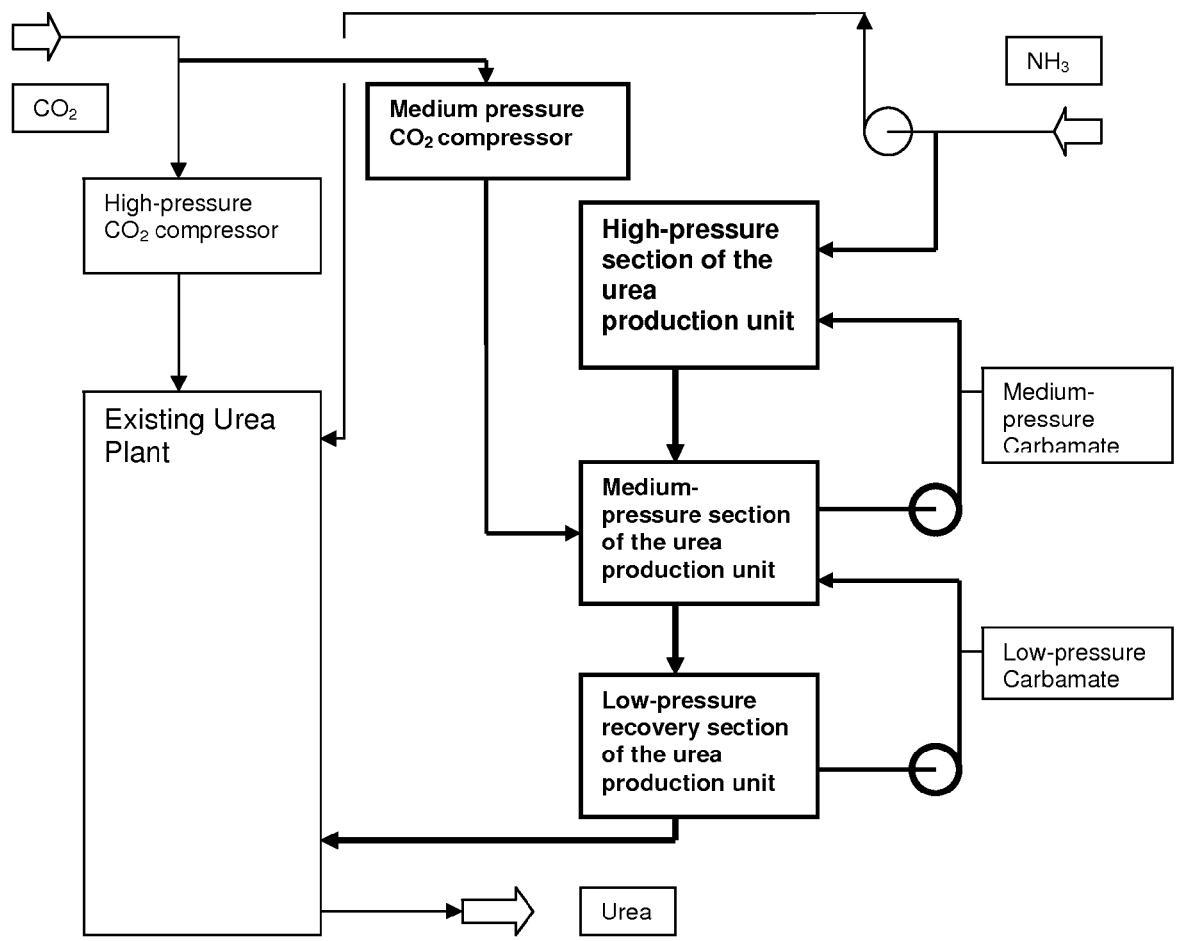

This application is the national phase of PCT application PCT/EP2009/053748 having an international filing date of 30 Mar. 2009, which claims benefit of European application No. 08006710.1 filed 2 Apr. 2008. The contents of the above patent applications are incorporated by reference herein in their entirety.

The invention is directed to a process for increasing the capacity of an existing urea plant, comprising a high-pressure urea synthesis section and one or more recovery sections.

Urea plants with a high-pressure urea synthesis section and one or more recovery sections are known in the prior art.

In Ullman's Encyclopedia of Industrial Chemistry, 1996, Vol. A27, p. 346-350 the Snamprogetti process, the ACES process and the IDR process are described. These urea production processes contain both a medium-pressure and a low-pressure recovery section.

Further the Stamicarbon $CO_2$-stripping process is described containing a high-pressure synthesis section and a low-pressure recovery section. Also in WO-02/090323 a urea production process is described containing a high-pressure synthesis section and medium- and low-pressure recovery sections. According to this patent publication a urea synthesis solution is prepared at high-pressure in a urea reactor from ammonia and carbon dioxide. A part of this urea synthesis solution is transferred from the high-pressure reactor to a medium-pressure treatment section. Another part of the urea synthesis solution is treated further in the high-pressure stripper and is thereafter sent to the low-pressure recovery section.

In this patent publication is also described that the medium-pressure treatment zone can be additionally installed to increase the capacity of an existing urea plant. A disadvantage of the installation of only a medium-pressure treatment zone to an existing urea plant is that no extra reactor volume is added to the existing plant. Because of this, the increase in capacity for the existing urea plant is limited.

Another disadvantage is that the existing high-pressure carbon dioxide compressor has to be modified to realize a substantial plant capacity increase and that this modification is very costly.

It is the object of the present invention to overcome these disadvantages and to provide a process for increasing the capacity of an existing urea plant in the most efficient and cost effective way.

This object is achieved by the installation, next to the existing urea plant, of a urea production unit, comprising a high-pressure urea synthesis section and a medium-pressure recovery section, wherein a urea-containing stream is produced from ammonia and carbon dioxide and the urea-containing stream is sent to the existing urea plant where the urea-containing stream is further purified in the low-pressure recovery section.

This has the advantage that a capacity increase of 30-100% of the existing plant can be obtained.

The urea production unit can also contain a low-pressure recovery section and a urea-containing stream is then transported from the low-pressure recovery section of the urea production unit to the finishing section of the existing urea plant and is treated in the finishing section to produce urea particles.

It is, of course, also possible to construct a new finishing section next to the already existing finishing section.

A carbamate stream is transported from the low-pressure recovery section to the medium-pressure recovery section of the urea production unit. The low-pressure recovery section can be the low-pressure recovery section of the existing plant and the low-pressure recovery section of the urea production unit. A urea production unit comprises a high-pressure synthesis section.

The high-pressure section can comprise a reactor in which the urea synthesis solution is prepared, a stripper in which the urea synthesis solution is stripped, a condenser in which the gases released in the stripping zone are condensed and a scrubber in which ammonia and carbon dioxide are removed from the synthesis gas. The synthesis can be carried out in a single reactor or in two reactors.

When use is made of two reactors, the first reactor can, for example, be operated using virtually fresh raw materials and the second using raw materials entirely or partly recycled, for example from the urea recovery section.

Ammonia and carbon dioxide are fed to the reactor either directly or indirectly. Ammonia and carbon dioxide can be introduced to the urea production unit at various places in the high-pressure synthesis section or to the recovery sections. Preferably, ammonia is fed directly to the reactor. This to introduce heat into the reactor that is formed during the exothermal reaction between ammonia and carbon dioxide. To introduce more heat to the reactor the ammonia stream can be pre-heated.

In the stripper the urea synthesis solution can be stripped in counter current with ammonia and/or carbon dioxide with the supply of heat. It is also possible to use thermal stripping. Thermal stripping means that ammonium carbamate in the urea synthesis solution is decomposed and the ammonia and carbon dioxide present are removed from the urea solution exclusively by means of the supply of heat. Stripping may also be effected in two or more steps. The gas stream containing ammonia and carbon dioxide that is released from the stripper can be returned to the reactor, optionally via a high-pressure carbamate condenser.

The gas mixture obtained in the stripper can be condensed and absorbed in a high-pressure carbamate condenser, following which the resulting ammonium carbamate can be transferred to the reactor for the formation of urea.

The high-pressure condenser can for example be a falling-film condenser or a so-called submerged condenser as described in NL-A-8400839. The submerged condenser can be placed horizontally or vertically.

The synthesis gas that has not reacted in the reactor can be removed from the reactor or can be sent to a high-pressure scrubber. In a high-pressure scrubber the condensable components, ammonia and carbon dioxide, can be absorbed from the synthesis gas into a carbamate stream from the medium-pressure recovery section or from the low-pressure recovery section. This scrubbing process in the high-pressure scrubber can be stimulated by using a heat exchanger that extracts heat from the process. The carbamate stream from the high-pressure scrubber can be returned to the reactor, optionally via the high-pressure carbamate condenser.

In the high-pressure synthesis section the pressure is substantially equal to the urea synthesis pressure in the reactor, which is the pressure at which urea formation takes place. The urea synthesis pressure is usually a pressure between 11-40 MPa, preferably 12.5-19 MPa. The pressure in the rest of the high-pressure section is substantially equal to the pressure in the reactor. Substantially equal means that the pressure in the rest of the high-pressure section is less than 1.5 MPa higher or lower than in the reactor.

An oxidizing agent is added to the urea production unit in order to protect the materials of construction against corrosion. An oxide skin is formed on the metal parts, which protects against corrosion. This process is known as passivation. The passivating agent may be oxygen or an oxygen-releasing compound as described in for example U.S. Pat. No. 2,727,069. Oxygen can be added, for instance, in the form of air or as a peroxide.

Preferably, the high-pressure section of the urea production unit comprises only a reactor and a stripper. This to limit the amount of expensive high-pressure equipment present in this section.

More preferably, the stripper in the high-pressure section of the urea production unit is a thermal stripper and passivation air is introduced to the stripper. The stripper is preferably a thermal stripper, because in the urea production unit, preferably no high-pressure carbon dioxide is available. In the urea production unit carbon dioxide is preferably added, as explained further on, via a medium-pressure carbon dioxide compressor.

The reactor and the stripper in the urea production unit can be made of a an austenitic-ferritic duplex steel with a chromium content of between 26 and 35 wt. % and a nickel content of between 3 and 10 wt %. This type of steel is less corrosion sensitive. When this type of steel is used for the construction of the reactor and the stripper it is possible to omit the introduction of passivation air to the urea production unit.

In the recovery section ammonia and carbon dioxide that did not react to form urea are recovered from the urea-comprising stream, produced in the high-pressure synthesis section, in order to be recycled to the high-pressure section. In the recovery sections the pressure is lower than in the high-pressure synthesis section. In the urea production unit according to the present invention at least a medium-pressure recovery section is present.

When more than one recovery section is present at least one of the recovery sections is operated at medium pressure and one at low pressure.

Medium pressure is a pressure between 1.0 and 8.0 MPa, preferably between 1.2 and 3.0 MPa. Low pressure is a pressure between 0.2 and 0.8 MPa, preferably between 0.3 and 0.5 MPa.

The medium-pressure recovery section of the urea production unit can comprise a medium-pressure carbon dioxide compressor, a medium-pressure decomposer, a medium-pressure scrubber and a medium-pressure carbamate condenser. Preferably, the medium-pressure recovery section comprises a carbon dioxide compressor, a decomposer and a carbamate condenser. In the carbamate condenser the released condensation heat can be used for concentrating the urea-containing stream and/or the heat can be released in a cooling water system.

When the carbon dioxide is introduced in the urea production unit at medium-pressure it is possible to use a medium-pressure carbon dioxide compressor instead of a high-pressure carbon dioxide compressor. This remarkably reduces the investment to be made for the construction of the urea production unit. Preferably, the carbon dioxide is fed to the medium-pressure carbamate condenser.

To the medium-pressure carbamate condenser also a low-pressure carbamate stream is added coming from the low-pressure recovery section present in the urea production unit or from the low-pressure recovery section present in the existing urea plant. In the medium-pressure carbamate condenser a medium-pressure carbamate stream is formed. This medium-pressure carbamate stream is, preferably, fed directly to the reactor and/or the stripper in the high-pressure synthesis section. This in order to introduce the carbon dioxide directly to the reactor and to promote heating of the reactor.

In the low-pressure recovery section of the urea production unit or of the existing urea plant the urea-containing stream(s) coming from the high-pressure synthesis section of the existing plant and/or from the medium-pressure recovery section(s) of the existing plant and/or the urea production unit almost all the residual non-converted ammonia and carbon dioxide are removed from the urea synthesis solution. When the urea production unit also contains a low-pressure recovery section the urea-containing stream is transported to the finishing section of the existing urea plant. In the finishing section urea particles are produced. Urea particles can be produced, for instance, by prilling or granulation.

The invention is also directed to a urea production unit for the production of urea from ammonia and carbon dioxide installed next to an existing urea plant, comprising a high-pressure urea synthesis section and a medium-pressure recovery section wherein the medium-pressure recovery section of the urea production unit is connected to the low-pressure recovery section of the existing urea plant.

The urea production unit can also contain a low-pressure recovery section and in these urea production units the low-pressure recovery section of the urea production unit is connected to the finishing section of the existing urea plant.

A schematic overview of the connections between the existing urea plant and the urea production unit is given in FIG. 1.

The invention will be further explained in the examples, without being limited thereto.

EXAMPLE I

Figure 2:
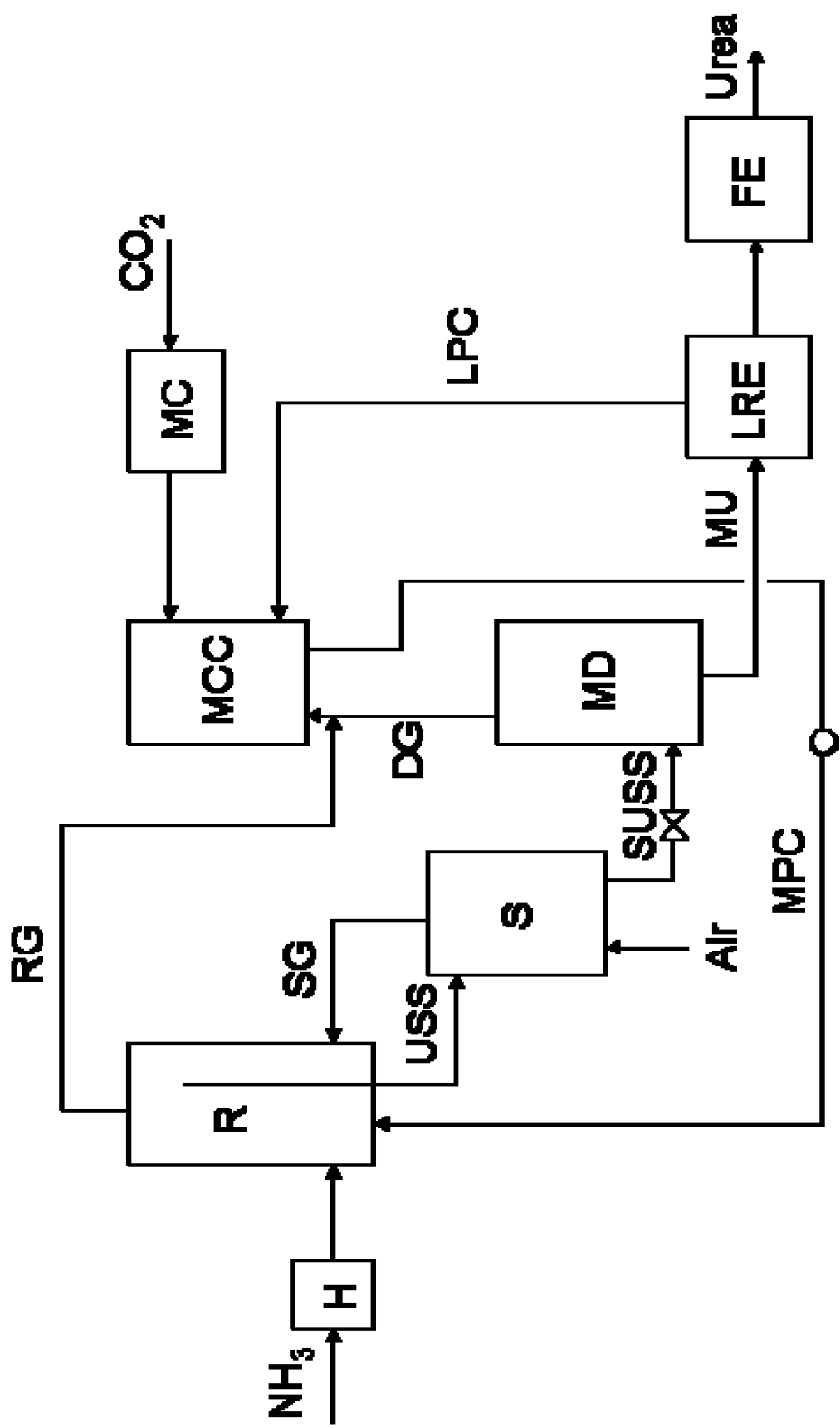

FIG. 2 schematically represents a urea production unit according to the invention.

Ammonia is preheated in heater H and fed to the reactor R of the urea production unit. In the urea production unit a urea-containing stream USS is produced that is stripped in thermal stripper S. In the stripper a small amount of passivating air is introduced and strip gases SG containing unreacted ammonia and carbon dioxide are returned to the reactor. The stripped urea-containing stream SUSS is reduced in pressure and introduced into a medium-pressure decomposer MD. In the medium-pressure decomposer a further purified urea-containing stream is obtained MU which is sent to the low-pressure recovery section of an existing urea plant LRE and from there to the finishing section of the existing urea plant FE, where urea particles are formed. In the low-pressure recovery section of the existing urea plant a low-pressure carbamate stream LPC is produced, which is sent to the medium-pressure carbamate condenser MCC of the medium-pressure recovery section of the urea production unit. In the MCC carbon dioxide is introduced via a medium-pressure carbon dioxide compressor MC. In the MCC also the gas streams coming from the reactor RG and the medium-pressure decomposer DG are introduced. In the MCC a medium-pressure carbamate stream MPC is formed which stream is, via a pump, returned to the reactor.

The invention claimed is:

1. A system for increasing the capacity of an existing urea plant, said existing urea plant comprising a first high-pressure urea synthesis section, one or more low-pressure recovery sections and a finishing section, wherein a urea production unit comprising a second high-pressure urea synthesis section and a medium-pressure recovery section is installed next to the existing urea plant, and wherein a urea-containing stream is produced in said second high-pressure urea synthesis section from ammonia and carbon dioxide and the urea-containing stream is sent to the existing urea plant where the urea-containing stream is further purified in the low-pressure recovery section.

2. The system according to claim 1, wherein the urea production unit also contains a low-pressure recovery section, wherein a urea-containing stream is transported from the low-pressure recovery section of the urea production unit to the finishing section of the existing urea plant and is treated in the finishing section to produce urea particles.

3. The system according to claim 1, wherein a carbamate stream is transported from the low-pressure recovery section of the existing urea plant to the medium-pressure recovery section of the urea production unit.

4. The system according to claim 1, wherein the second high-pressure urea synthesis section comprises a reactor and a stripper.

5. The system according to claim 4, wherein the stripper is a thermal stripper and that passivation air is introduced to the stripper.

6. The system according to claim 4, wherein the reactor and the stripper are made of a an austenitic-ferritic duplex steel with a chromium content of between 26 and 35 wt. % and a nickel content of between 3 and 10 wt %.

7. The system according to claim 1, wherein the medium-pressure recovery section comprises a medium-pressure carbon dioxide compressor and a medium-pressure carbamate condenser.

8. The system according to claim 7, wherein carbon dioxide is fed to the medium-pressure carbon dioxide compressor and from there to the medium-pressure carbamate condenser, where the carbon dioxide is absorbed in a low-pressure carbamate stream forming a medium-pressure carbamate stream.

9. The system according to claim 8, wherein the second high-pressure synthesis section comprises a reactor and a stripper and wherein the medium-pressure carbamate stream is transported from the medium-pressure carbamate condenser to the reactor and/or the stripper in the high-pressure synthesis section.

10. The system according to claim 4, wherein ammonia is fed to the reactor in the high-pressure synthesis section.

11. The system according to claim 10, wherein ammonia is heated before it is fed to the reactor in the second high-pressure synthesis section.

12. A urea production unit for the production of urea from ammonia and carbon dioxide installed next to an existing urea plant said existing urea plant comprising at least a low pressure recovery section and a finishing section, said production unit comprising a high-pressure urea synthesis section and a medium-pressure recovery section wherein the medium-pressure recovery section of the urea production unit is connected to the low-pressure recovery section of the existing urea plant.

13. A urea production unit according to claim 12, wherein the urea production unit also contains a low-pressure recovery section and wherein the low-pressure recovery section of the urea production unit is connected to the finishing section of the existing urea plant.

* * * * *

UNITED STATES PATENT AND TRADEMARK OFFICE
CERTIFICATE OF CORRECTION

PATENT NO. : 8,377,399 B2  
APPLICATION NO. : 12/936190  
DATED : February 19, 2013  
INVENTOR(S) : Johannes Henricus Mennen Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 229 days.

Signed and Sealed this

First Day of September, 2015

Michelle K. Lee  
*Director of the United States Patent and Trademark Office*